United States Patent
Senn et al.

(10) Patent No.: US 9,833,508 B2
(45) Date of Patent: Dec. 5, 2017

(54) CANCER THERAPEUTICS

(71) Applicant: IMMIX CORPORATION, Los Angeles, CA (US)

(72) Inventors: Sean Senn, West Hills, CA (US); Ilya Rachman, Los Angeles, CA (US)

(73) Assignee: Immix Biopharma, Inc., Los Angeles, CA (US)

( * ) Notice: Subject to any disclaimer, the term of this patent is extended or adjusted under 35 U.S.C. 154(b) by 0 days.

(21) Appl. No.: 14/385,140

(22) PCT Filed: Mar. 15, 2013

(86) PCT No.: PCT/US2013/032153
§ 371 (c)(1),
(2) Date: Sep. 12, 2014

(87) PCT Pub. No.: WO2013/138735
PCT Pub. Date: Sep. 19, 2013

(65) Prior Publication Data
US 2015/0110877 A1 Apr. 23, 2015

Related U.S. Application Data

(60) Provisional application No. 61/611,529, filed on Mar. 15, 2012, provisional application No. 61/701,018, filed on Sep. 14, 2012.

(51) Int. Cl.
*A61K 39/395* (2006.01)
*A61K 9/107* (2006.01)
*A61K 31/12* (2006.01)
*A61K 31/713* (2006.01)
*A61K 45/06* (2006.01)
(Continued)

(52) U.S. Cl.
CPC ........ *A61K 39/3955* (2013.01); *A61K 9/1075* (2013.01); *A61K 31/12* (2013.01); *A61K 31/713* (2013.01); *A61K 47/6907* (2017.08); *C07K 16/28* (2013.01); *A61K 9/107* (2013.01);
(Continued)

(58) Field of Classification Search
None
See application file for complete search history.

(56) References Cited

U.S. PATENT DOCUMENTS

2007/0253899 A1* 11/2007 Ai .................. A61K 9/1075
424/1.37
2010/0260677 A1* 10/2010 Bhatia ............. A61K 41/0052
424/9.1

FOREIGN PATENT DOCUMENTS

WO  WO 2011/038110  *  3/2011 ........... A61K 39/395
WO  WO 2011/130486 A2 * 10/2011 ........... A61K 31/192

OTHER PUBLICATIONS

Rastogi et al., "Glut-1 antibodies induce growth arrest and apoptosis in human cancer cell lines", Cancer Letters, 257, pp. 244-251 (2007).*

* cited by examiner

*Primary Examiner* — Bethany Barham
*Assistant Examiner* — Barbara Frazier
(74) *Attorney, Agent, or Firm* — Archer Norris, PLC; Sean D. Senn

(57) ABSTRACT

The invention relates to the treatment of cancer. In one embodiment, the present invention provides a composition comprising a micelle construct attached to a glut-1 antibody and a curcumin molecule. In another embodiment, the present invention provides a method of treating colon and/or breast cancer by administering a therapeutically effective
(Continued)

amount of composition comprising a targeted construct attached to an inhibitor of NF-kB.

6 Claims, 11 Drawing Sheets

(51) Int. Cl.
 *A61K 39/00* (2006.01)
 *C07K 16/28* (2006.01)
 *C12N 15/113* (2010.01)
 *A61K 47/69* (2017.01)
(52) U.S. Cl.
 CPC ........ *C12N 15/113* (2013.01); *C12N 2310/14* (2013.01); *Y10T 428/2982* (2015.01)

Figure 2.

| 72 hour test | Ab + siRNA (ug/ml) | | | | | |
|---|---|---|---|---|---|---|
| | 31.7+8.3 | 6.34 + 1.66 | 1.268 + 0.332 | 0.2536 + 0.0664 | 0.05072 + 0.01328 | 0.00 |
| HCT-116 | 1.09 | 1.23 | 1.29 | 1.30 | 1.19 | 1.18 |
| | 1.18 | 1.29 | 1.32 | 1.25 | 1.20 | 1.24 |
| | 1.08 | 1.23 | 1.21 | 1.28 | 1.29 | 1.24 |
| | 1.08 | 1.22 | 1.20 | 1.21 | 1.18 | 1.11 |
| MDA-MB-231 | 0.70 | 0.79 | 0.77 | 0.78 | 0.76 | 0.87 |
| | 0.78 | 0.84 | 0.84 | 0.83 | 0.78 | 0.71 |
| | 0.78 | 0.82 | 0.85 | 0.85 | 0.84 | 0.74 |
| | 0.76 | 0.79 | 0.84 | 0.81 | 0.82 | 0.84 |

Cell viability ratio = 100 * (OD test / OD control-0)

| 72 hour test | Ab + siRNA (ug/ml) | | | | | |
|---|---|---|---|---|---|---|
| | 31.7+8.3 | 6.34 + 1.66 | 1.268 + 0.332 | 0.2536 + 0.0664 | 0.05072 + 0.01328 | 0.00 |
| HCT-116 | 91.28 | 103.49 | 108.14 | 108.87 | 99.97 | 1.19 |
| | 99.34 | 108.47 | 110.74 | 104.83 | 100.69 | |
| | 90.97 | 103.59 | 101.74 | 107.95 | 108.59 | |
| | 91.09 | 102.45 | 101.16 | 101.39 | 98.93 | |
| MDA-MB-231 | 88.39 | 100.48 | 97.03 | 98.41 | 95.55 | 0.79 |
| | 98.85 | 106.28 | 106.02 | 104.54 | 99.00 | |
| | 98.82 | 103.81 | 107.67 | 107.50 | 105.61 | |
| | 95.82 | 99.32 | 106.13 | 102.60 | 103.92 | |

(A)

(B)

SEQUENCE LISTING

```
<160> NUMBER OF SEQ ID NOS: 2

<210> SEQ ID NO 1
<211> LENGTH: 19
<212> TYPE: RNA
<213> ORGANISM: Homo sapiens

<400> SEQUENCE: 1
gcccuauccc uuuacguca                                                19

<210> SEQ ID NO 2
<211> LENGTH: 19
<212> TYPE: RNA
<213> ORGANISM: Homo sapiens

<400> SEQUENCE: 2
ugacguaaag ggauagggc                                                19
```

CANCER THERAPEUTICS

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

In 2010 alone, it is estimated that 569,490 men and women will die of cancer, with an additional 1,529,560 men and women diagnosed. However, despite billions of dollars spent in cancer research, complete and effective treatments for this terrible disease have still not been developed. Part of the reason is because tumor cells may be made up of a variety of cell types, produced as the cells proliferate and incur different mutations. This diversity, in turn, is part of what has made treatment of cancer so difficult, as a population of cancerous cells could easily include a mutant variety that happens to be resistant to any individual treatment or chemotherapy drug that is administered. The few resistant cancer cells are provided a strong selective advantage in comparison to other cells, and over time, those resistant cells increase in frequency. An effective cancer treatment would therefore benefit from attacking the cancer early, as well as attacking aggressively. This could come in the form of administering a combination of drugs for treatment, as the odds of a single cell being resistant to a larger quantity of drugs is lower. Additionally, an effective cancer treatment could also potentially bypass the diversity of cancer cells by targeting processes that cancer cells rely on for their very growth. One such process is tumors' reliance on producing and processing sugar for its cell growth. Thus, there is a need in the art for the development of additional cancer treatments, including those that have the ability to better target drug resistant tumors.

BRIEF DESCRIPTION OF THE FIGURES

Exemplary embodiments are illustrated in referenced figures. It is intended that the embodiments and figures disclosed herein are to be considered illustrative rather than restrictive.

FIG. 2 depicts, in accordance with an embodiment herein, results of MTT viability assays of both HCT-116 and MDA-MB-231 cells after administration of a composition comprising glut-1 Ab and NF-kB siRNA.

FIG. 7(A) depicts micellar combination treatment, with DOX constant, and Curcumin variable, applied over 48 hours to breast cancer (MDA-MB231 cell line). FIG. 7(B) depicts micellar combination treatment, with DOX constant, and GLUT1-Curcumin variable, applied over 48 hours to breast cancer (MDA-MB231 cell line). There is an increase in effectiveness of treatment of breast cancer using the GLUT1-Curcumin compound in micelles.

BRIEF SUMMARY OF THE INVENTION

Figure 1:
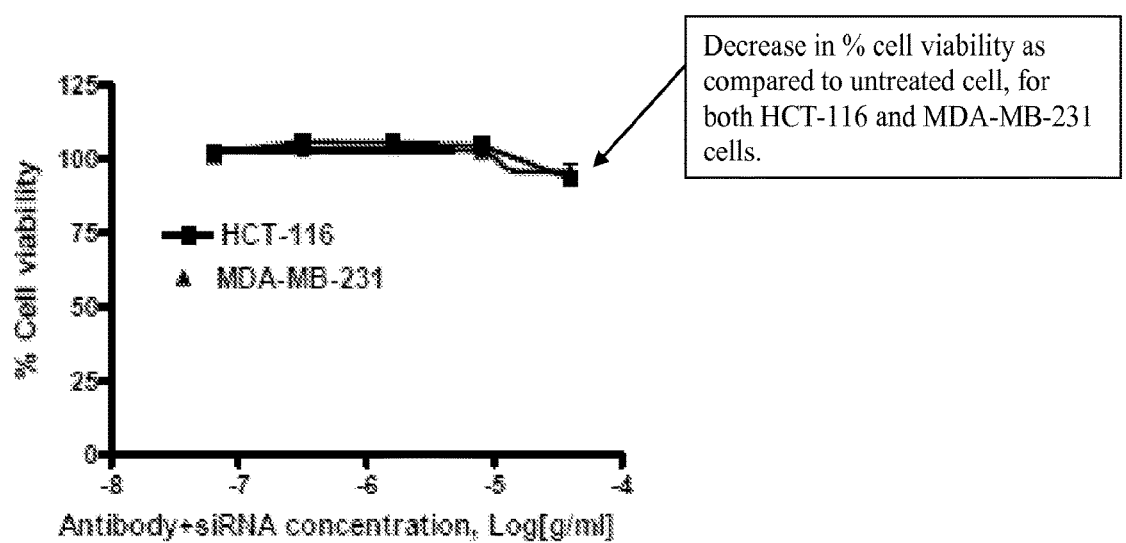
FIG. 1 depicts, in accordance with an embodiment herein, a graph of the effects of test samples on the growth of HCT-116 and MDA-MB-231 cells as determined by MTT viability assay. Specifically, target cells were seeded into 96-well plate at a density of 5,000/well and then were incubated at 37° C./5% CO2 overnight (20 hours) to allow the cells to adhere. Test samples (2× stock solution) at various concentrations were added in quadruplicate and the cells were incubated at 37° C./5% CO2 for 48 h/72 h. Cell viability was evaluated with MTT assay. The absorbance of each well (O.D. at 540 nM) was measured in MTT viability assay and data was presented as percentage of cell viabilities as compared with the non-treated cells. The graph depicts the results of administration of a composition of both the siRNA and Ab after 72 hours from administration. At a concentration higher than −5, such as 31.7 ug/ml glut-1 Ab and 8.3 ug/ml NF-kB siRNA, it appears that both the HCT-116 and MDA-MB-231 cells have a decrease in % of cell viability as compared to non-treated cells.
Figure 3:
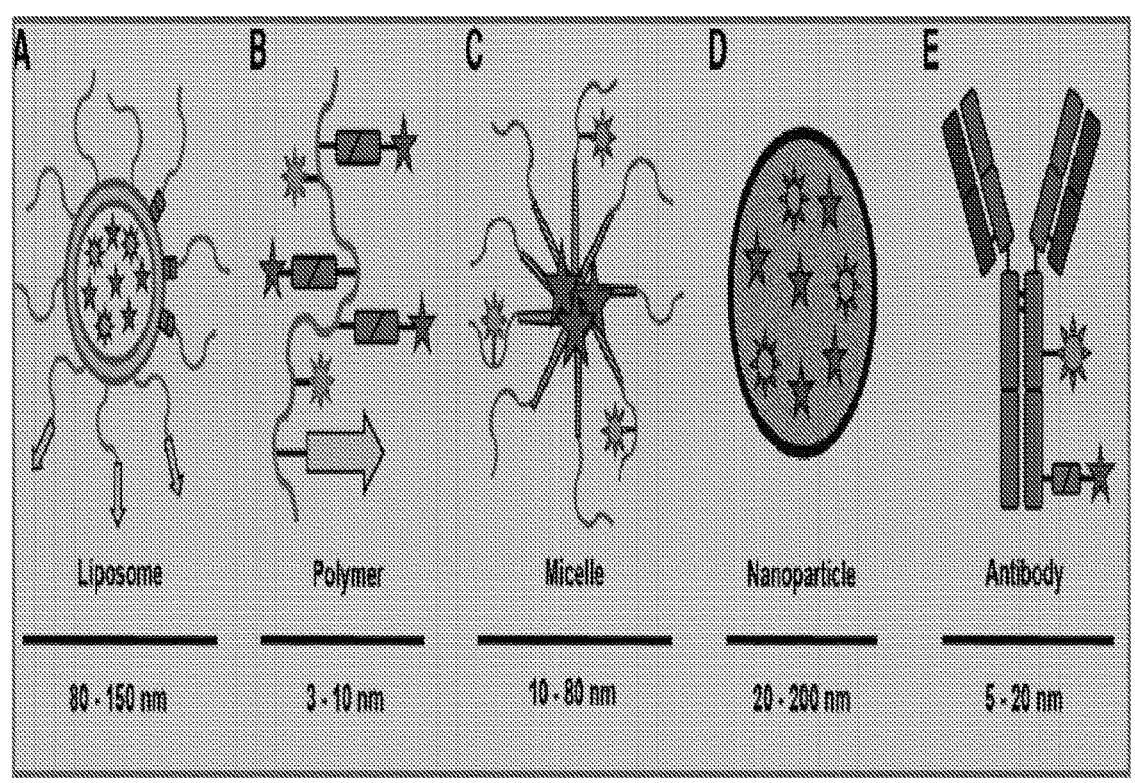
FIG. 3 (prior art) depicts examples of structures that may target drugs to tumors, although the present invention is in no way limited to these structures alone.
Figure 4:
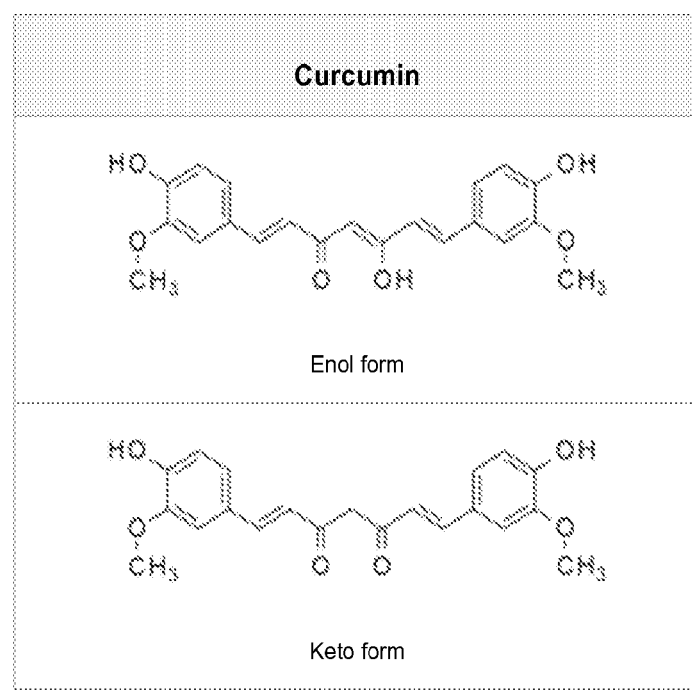
FIG. 4 depicts (prior art) examples of structures of curcumin.
Figure 5:
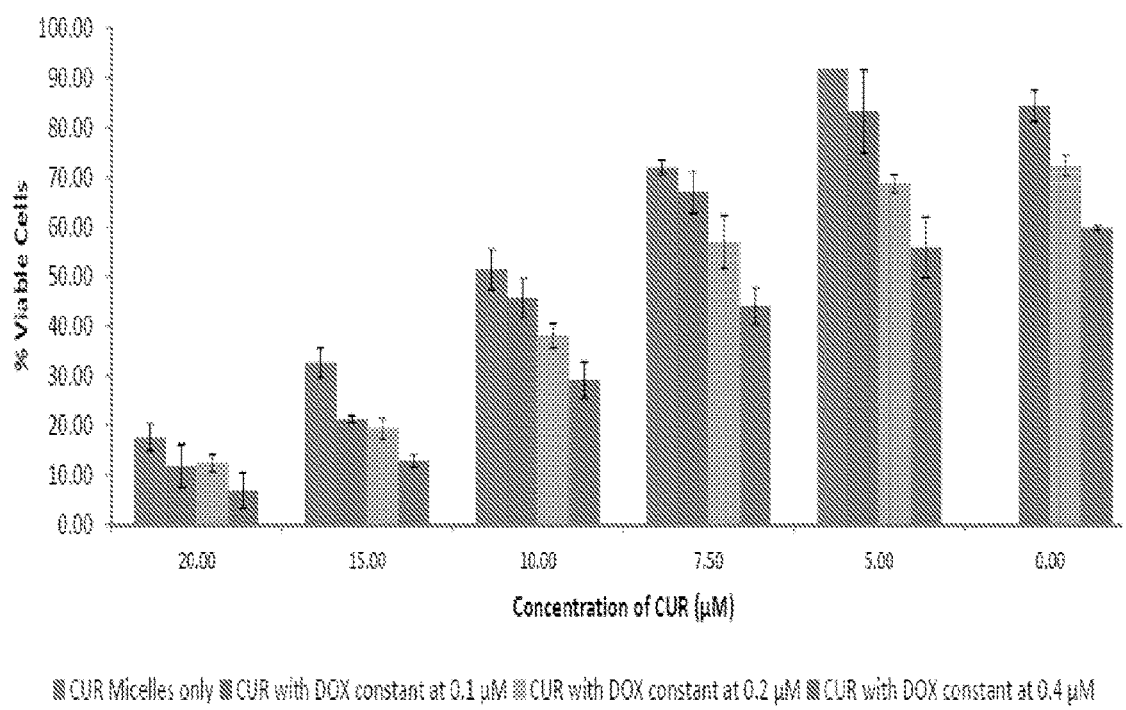
FIG. 5 depicts, in accordance with an embodiment herein, round A study of micellar combination treatment, with DOX constant, GLUT1-CUR variable, applied over 48 hours to HCT-116 cell line. The study demonstrates that the addition of the GLUT-1 antibody onto Curcumin micelles, in the presence of DOX in the system, produces significant enhancement to the toxicity, and demonstrates that the combination treatment is more effective than if applied in isolation.
Figure 6:
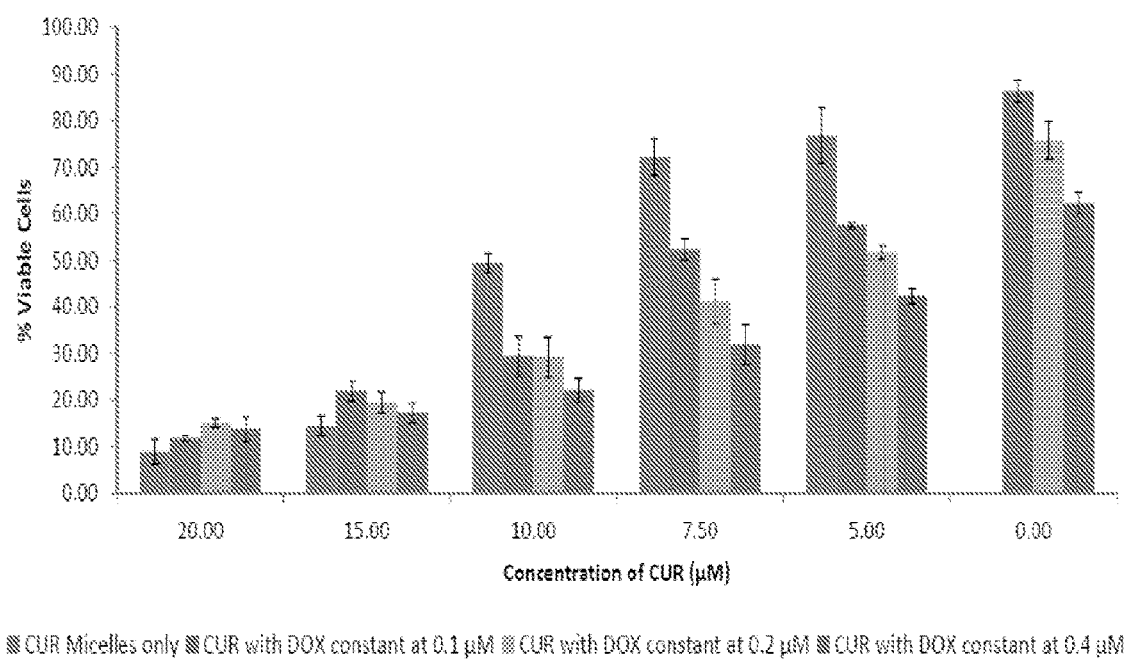
FIG. 6 depicts, in accordance with an embodiment herein, round B study of micellar combination treatment, with DOX constant, GLUT1-CUR variable, applied over 48 hours to colon cancer (HCT-116 cell line). The replication study further supports the finding that the addition of the GLUT-1 antibody onto Curcumin micelles, in the presence of DOX in the system, produces significant enhancement to the toxicity, and further demonstrates that the combination treatment is more effective than if applied in isolation.
Figure 7:
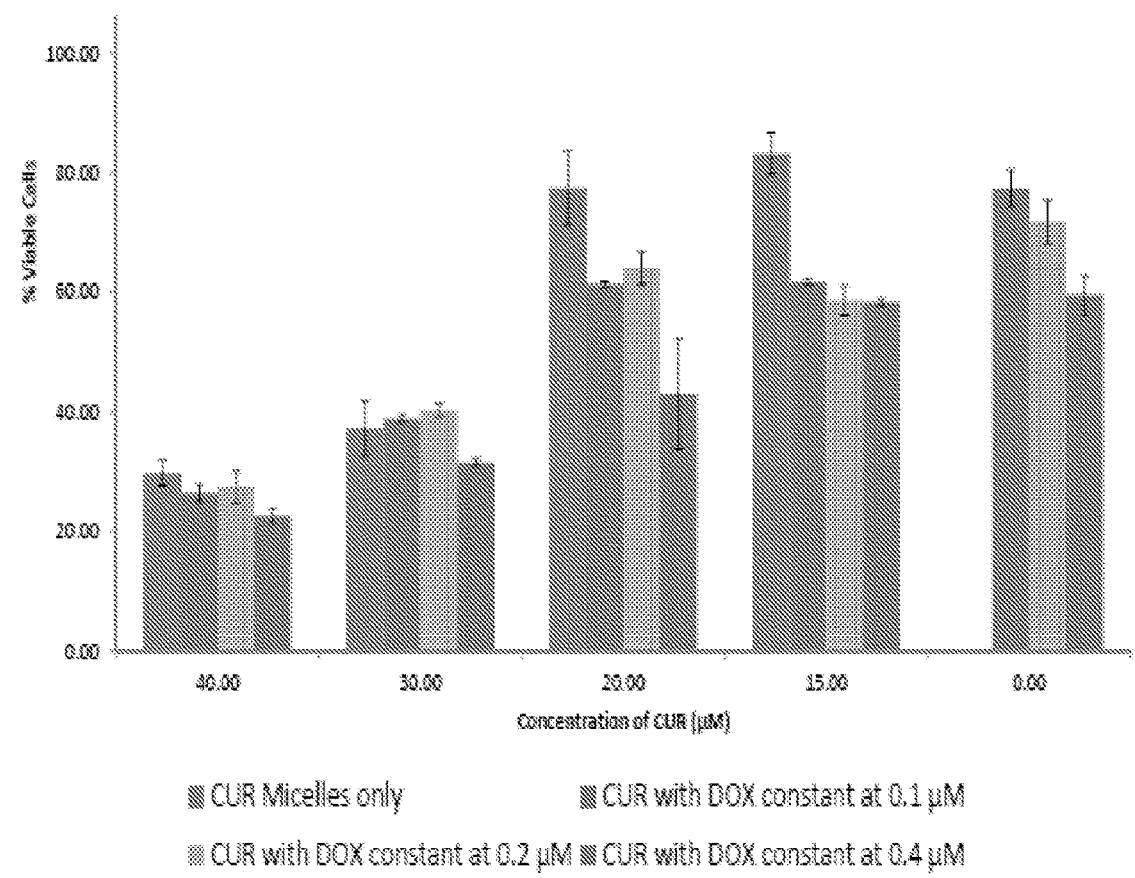
FIG. 7 depicts, in accordance with an embodiment herein, treatment of breast cancer (MDA-MB231 cell line).
Figure 7:
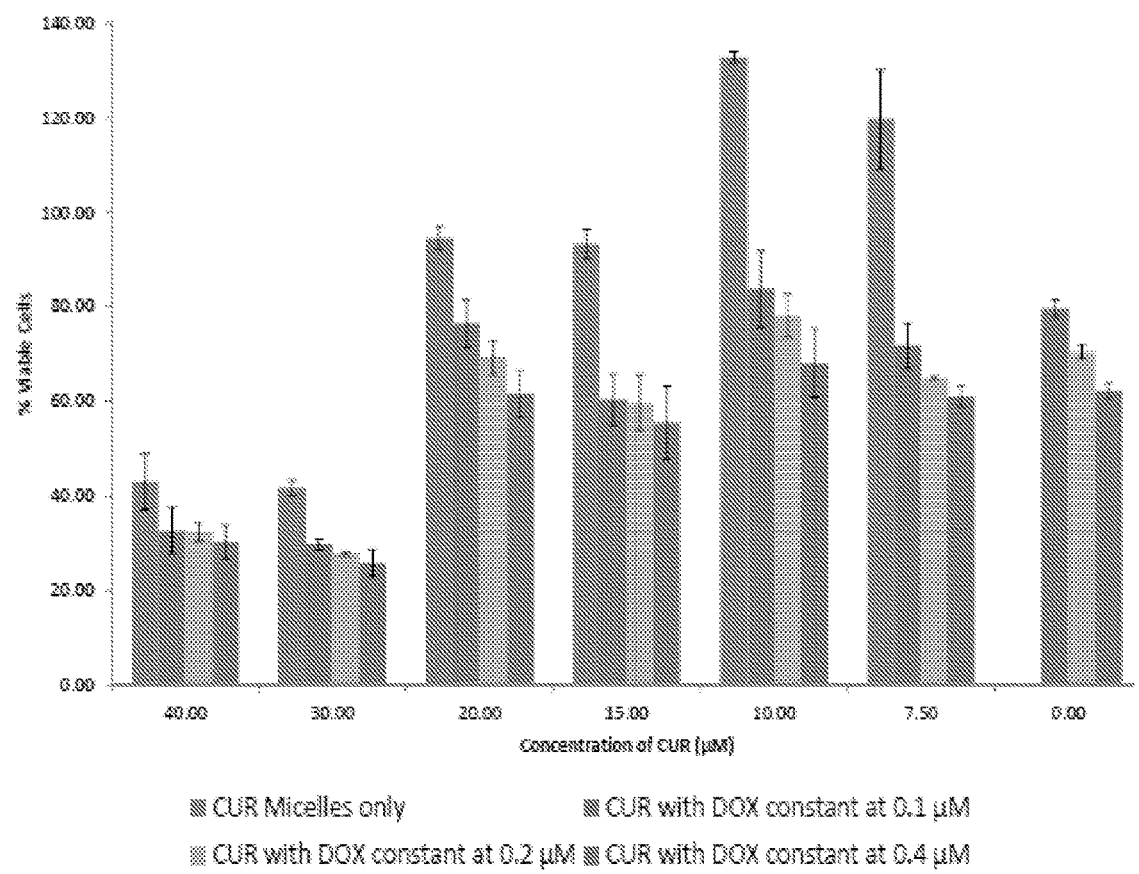
Figure 8:
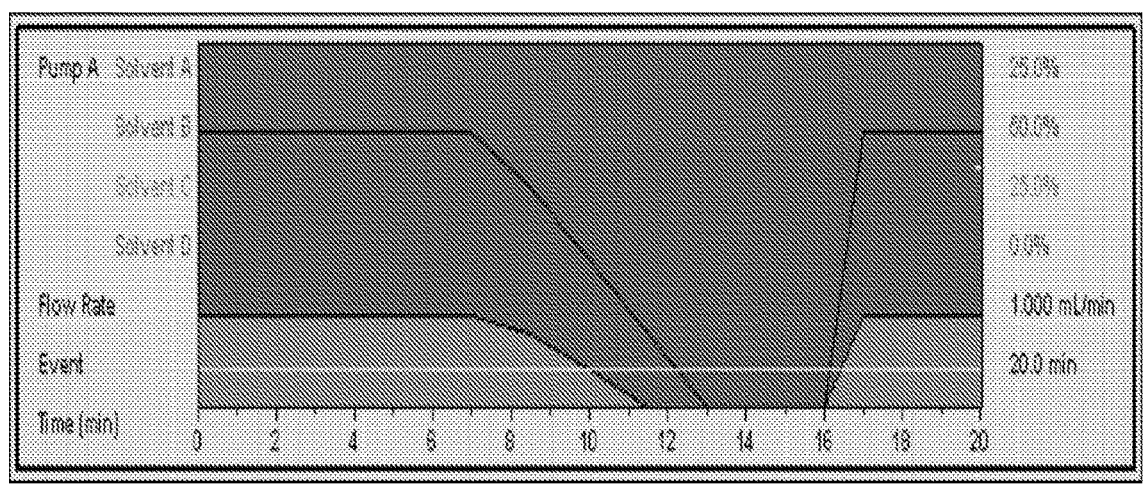
FIG. 8 depicts, in accordance with an embodiment herein, the gradient used in the HPLC method for analysis of DOX and CUR incorporation.
Figure 9:
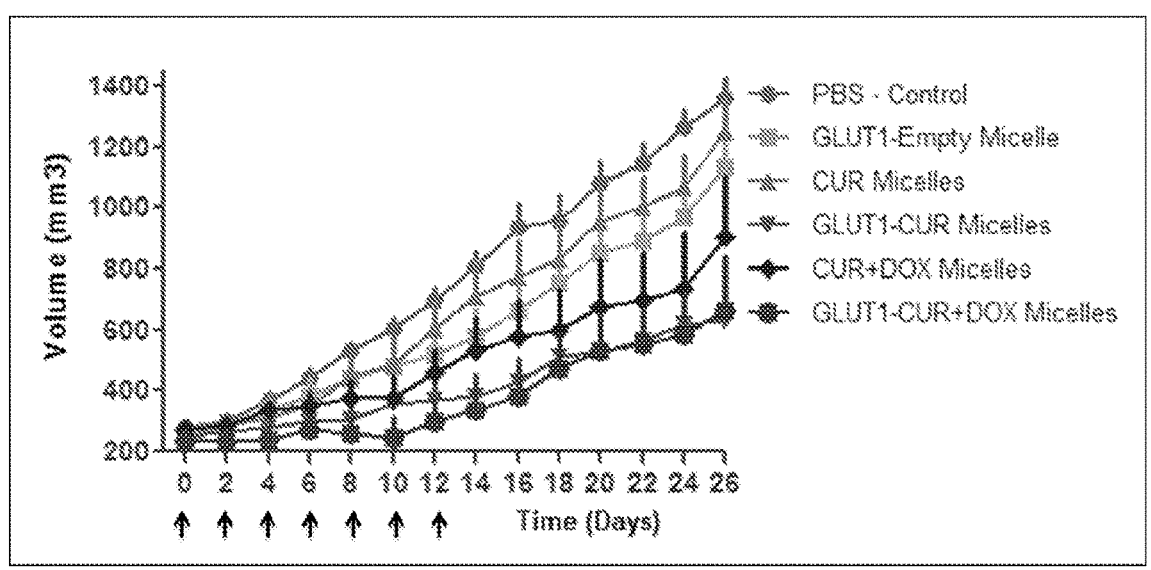
FIG. 9 depicts, in accordance with an embodiment herein, a chart of a in vivo study of Glut1-CUR+DOX constructs using HCT-116 cell line. Nude mice bearing ~250 mm$^3$ HCT-116 tumors were treated every 2 days starting at Day 0 (7 total IV injections) at a dose of 4 mg/kg CUR and 0.4 mg/kg DOX. N=6 with SEM.
Figure 10:
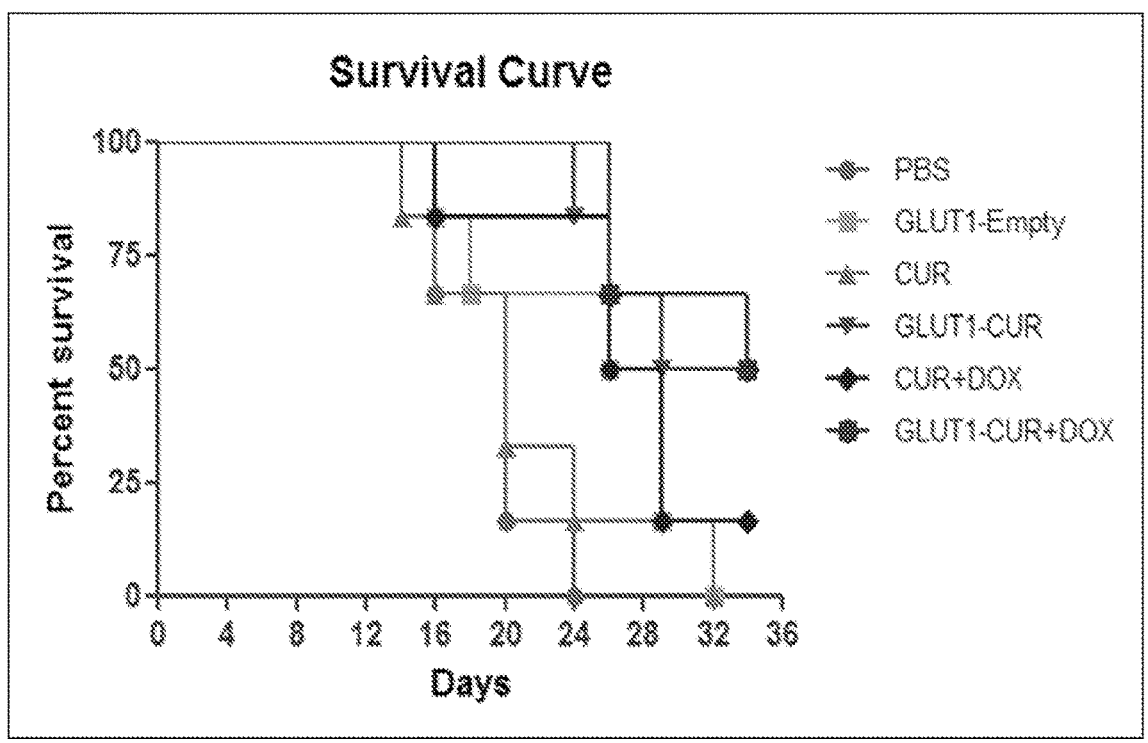
FIG. 10 depicts, in accordance with an embodiment herein, a survivor curve chart of the in vivo study of Glut1-CUR+DOX constructs using HCT-116 cells lines described in FIG. 9 and herein. Nude mice bearing ~250 mm$^3$ HCT-116 tumors were treated every 2 days starting at Day 0 (7 total IV injections) at a dose of 4 mg/kg CUR and 0.4 mg/kg DOX. N=6 with SEM. Survival was determined when the tumor reached 1000 mm$^3$. One way ANOVA with Tukey's post test showed that GLUT1-CUR and GLUT1-CUR+DOX were significantly different from PBS control group. Also, GLUT1-CUR+DOX was significantly different from the CUR group. (p<0.05). Two way ANOVA resulted in the following (p<0.05): PBS is significantly different from: GLUT1-CUR beginning at day 14, CUR+DOX at day 20, and GLUT1-CUR+DOX at day 12 till the end the study. GLUT1-Empty is significantly different from: GLUT1-CUR at day 26 and GLUT1-CUR+DOX at day 24 and 26. CUR is significantly different from: GLUT1-CUR beginning at day 20 and GLUT1-CUR+DOX at day 14 till the end the study.

Various embodiments include a method of treating cancer in a subject, comprising providing a composition comprising a micelle construct attached to an inhibitor of NF-kB, and administering a therapeutically effective dosage of the composition to the subject. In one embodiment, the micelle construct is targeted. In another embodiment, the micelle construct is targeted to bind to glut-1. In another embodiment, the micelle construct is less than 30 nm. In another embodiment, the inhibitor of NF-kB is curcumin, or a pharmaceutical equivalent, analog, derivative, and/or salt thereof. In another embodiment, the inhibitor of NF-kB is an siRNA molecule. In another embodiment, the composition further comprises one or more chemotherapy agents. In another embodiment, the micelle construct is further attached to one or more dox molecules. In another embodiment, the subject is a human. In another embodiment, the subject is a mouse. In another embodiment, the cancer is colon cancer. In another embodiment, the cancer is breast cancer.

Other embodiments include a pharmaceutical composition, comprising an inhibitor of NF-kB, a glut-1 antibody, and a pharmaceutically acceptable carrier. In another embodiment, the inhibitor of NF-kB is an siRNA molecule. In another embodiment, the glut-1 antibody is toxic. In another embodiment, the inhibitor of NF-kB is therapeutically effective amount of a compound of the formula:

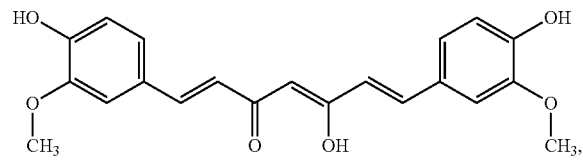

(Formula 1)

or a pharmaceutical equivalent, analog, derivative, and/or salt thereof. In another embodiment, the inhibitor of NF-kB is therapeutically effective amount of a compound of the formula:

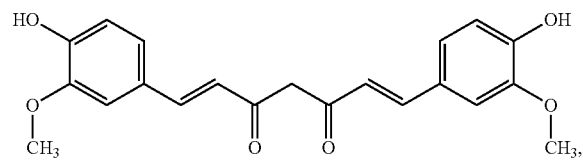

(Formula 2)

or a pharmaceutical equivalent, analog, derivative, and/or salt thereof. In another embodiment, the composition further comprises a micelle.

Other embodiments include a method of inhibiting cell growth of a tumor cell, comprising providing a composition comprising an antibody targeting Glut-1 and an inhibitor of NF-kB, wherein the antibody targeting Glut-1 and the inhibitor of NF-kB are conjugated to one another, and inhibiting cell growth by administering a therapeutically effective dosage to the tumor cell. In another embodiment, the inhibitor of NF-kB comprises siRNA. In another embodiment, the inhibitor of NF-kB comprises curcumin. In another embodiment, the inhibitor is at a concentration above 8.3 ug/ml. In another embodiment, the antibody targeting glut-1 is toxic. In another embodiment, the antibody targeting glut-1 is at a concentration above 31.7 ug/ml. In another embodiment, the tumor cell is a breast cancer and/or colon cancer cell type. In another embodiment, the composition further comprises a micelle.

Various embodiments include a nanoconjugate, comprising a targeting module for a mammalian glucose transporter, and an inhibitor of an inflammatory pathway mediator, where the targeting module for a mammalian glucose transporter and the inhibitor of an inflammatory pathway mediator are conjugated to one another. In another embodiment, the inflammatory pathway mediator comprises NF-kB. In another embodiment, the mammalian glucose transporter is a glut-1 receptor. In another embodiment, the nanoconjugate is between 20 nm and 50 nm. In another embodiment, the nanoconjugate is less than 60 nm. In another embodiment, the nanoconjugate is less than 20 nm. In another embodiment, the nanoconjugate is enclosed by a micelle.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

The term "nanoconjugate" may also include liposomal and micelle constructs.

The abbreviation "HCT-116" refers to a colon tumor cell line.

As used herein, "MDA-MB-231" refers to a breast tumor cell line.

As used herein, the abbreviation of "CUR" refers to curcumin.

As used herein, the term "DOX" refers to doxorubicin.

As readily apparent to one of skill in the art, various materials and methods are readily available and known to obtain curcumin and attach curcumin molecules to a construct or nanoconjugate in accordance with various embodiments herein. An example of curcumin may be a compound of the following formula:

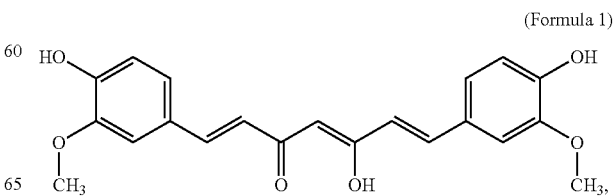

(Formula 1)

or a pharmaceutical equivalent, analog, derivative, and/or salt thereof.

In accordance with embodiments described herein, the inventors prepared various micelle compounds as cancer therapeutics. In one embodiment, the inventors prepared a cancer therapeutic construct based on a nano-sized lipid carrier encapsulating a cell-toxic chemotherapy molecule combined with an inhibitor of tumor chemo-resistance, targeted to tumor cells by tumor-recognizing antibody on its surface. Studies using chemotherapy-resistant colon and breast cancer lines in-vitro and in mouse xenografts showed significant tumor growth suppression, with almost no tumor growth seen (as compared to over 300% increase in tumor volume in control animals). Additionally, the construct was developed to be of optimal molecular size and biophysical properties in order to deliver clinically meaningful drug quantities in a whole animal setting, while avoiding toxicity associated with intravenous chemotherapy treatment.

In one embodiment, the effects of various components of therapeutic constructs were examined as follows: Mice were implanted subcutaneously with HCT-116 colon adenocarcinoma cells, and those in whom tumor mass volume reached 250 mm$^3$ were included. The animals with the implanted tumors were divided into six (6) groups (with 6 mice per group) and treated with one of the following:
1) Phosphate Buffered Saline (Control group)—(PBS Control)
2) Anti-Glut1 Antibody (Ab) linked to empty micelle—(Glut1-Empty Micelles)
3) Micelles containing Curcumin at a dose of 4 mg/kg—(Cur Micelles)
4) Anti-Glut1 Ab linked to Curcumin-containing micelles—(Glut1-Cur Micelles)
5) Micelles containing Doxorubicin (0.4 mg/kg) and Curcumin—(Cur+Dox Micelles)
6) The complete compound, Anti-Glut1 Ab linked to micelles containing Doxorubicin (0.4 mg/kg) and Curcumin Glut1-Cur+Dox Micelles.

As further disclosed herein, each group of mice was given 7 total intravenous injections every other day starting on Day 0. The tumor volume in each group of animals was measured on Day 12. Results were as follows:
1) The control group, treated with PBS only, showed a 180% increase in tumor volume on Day 12 as compared with Day 0
2) Glut1-Empty Micelles group showed a 100% increase in tumor volume
3) Cur Micelles group showed a 140% increase in tumor volume
4) Glut1-Cur Micelles group showed a 46% increase in tumor volume size
5) Cur+Dox Micelles group showed a 86% increase in tumor volume and
6) Glut1-Cur+Dox Micelles group showed just 6% increase in tumor volume.

The tumor inhibitory effects of various components were additive, with the complete compound showing the most dramatic, almost complete, inhibition of tumor growth at Day 12 time point. Importantly, the tumor inhibitory effect grew in size as each additional component was being added to the experimental construct. The inventors also demonstrated that the combination of anti-Glut1 Ab and curcumin-loaded micelles was the second most potent formulation in tumor growth suppression. Cur+Dox micelles and Glut1A-linked empty micelles showed similar tumor suppressing effect, at approximately ½ of the effect of the complete compound. The effect on tumor growth suppression observed in vivo paralleled very closely results obtained from additional in vitro studies by the inventors described herein. Specifically, the same additive effects of various compound components on tumor growth suppression were seen in vitro.

In one embodiment, the present invention provides a method of treating cancer and/or inhibiting growth in a tumor cell in a subject, by providing a composition comprising a micelle targeted by glut-1 receptor antibody and attached to curcumin and/or dox, and administering a therapeutically effective dosage to the subject. In another embodiment, the composition is administered to the subject intravenously.

In accordance with embodiments further described herein, by utilizing dox attached to a targeted micelle as a lipid-based delivery vehicle, rather than liposomal dox, or just dox, for example, the inventors created a cancer treatment with significantly high penetration of tumor mass. In addition to creating high tumor mass penetration, administering a composition comprising a dox attached to a targeted micelle optimized intracellular delivery of dox within the tumor cell itself. Because dox acts as a weakly basic compound, if it enters a low pH environment, or the lysosome of a tumor cell for example, the dox can lose much of its effectiveness for inhibiting tumor cell growth. By administering dox attached to a targeted micelle, rather than administering liposomal dox for example, the inventors enabled the dox to instead enter the cytoplasm, thus optimizing intracellular delivery. Additionally, dox can have high toxicity which can thus limit its practical application in vivo and usefulness as a cancer treatment for human subjects. In contrast, the inventors administered dox attached to a targeted micelle, resulting in further optimization of its effectiveness as a cancer therapeutic.

In accordance with various embodiments further disclosed herein, the inventors also attached curcumin to a targeted micelle. Due to its nonsoluble properties, if administered directly, curcumin must be administered at high concentrations to be effective inhibiting tumor growth. However, at those same high concentrations, curcumin results in high toxicity, thus making it an impractical and ineffective cancer treatment in vivo, and particularly difficult for use in human patients. In accordance with an embodiment herein, by attaching curcumin to a targeted micelle, treatment can be administered at a significantly lower dosage, thus reducing toxicity while effectively inhibiting tumor growth.

As compared to the liposomal forms of both doxorubicin and curcumin, a micellar preparation is of significantly smaller molecular size (10-20 nm vs. 80-150 nm liposomes) resulting in improved tumor mass penetration from the vascular bed, thus creating a more effective cancer therapeutic. Additionally, in accordance with an embodiment herein, the addition of the Glut-1 Ab to the micelle greatly increased its therapeutic efficacy over the un-targeted micelle preparations through improved intracellular delivery of its contents. Glut-1 presents an attractive extracellular target since it is one of the main glucose transporters involved in tumor glucose uptake. Solid tumors can take up glucose at much higher rates than do normal cells. Glycolysis represents a main source of energy and carbon building blocks for growing tumors. Thus, in accordance with an embodiment herein, a micelle construct with a Glut-1 Ab is an effective cancer therapeutic, as glut-1 overexpression will persist even in the face of tumor phenotypic evolution, and it will be difficult for tumors to mutate away from glut-1 overexpression and still retain their high growth potential. In regard to using glut-1 as the tumor targeting entity, by binding to the tumor membrane-overexpressed glut-1, various embodiments of therapeutic micelles described herein get endocytosed into the cytoplasm rather than the low-pH lysosome, thereby increasing the therapeutic efficacy of doxorubicin (which has much lower activity at low pH).

Since the tumor lines used in these experiments were doxorubicin-resistant, it was critical that curcumin delivery occurred contemporaneously with doxorubicin exposure in order for it to exert its tumoricidal effect. As NF-kappa B overexpression and its attendant apoptosis- and chemotherapy-resistance are present in advanced cancers, the inventors designed various embodiments herein to include an NF-kappa B inhibitor (for example, curcumin) in order to unlock the cidal effect of doxorubicin. In one embodiment, the present invention is a tumor-targeted micelle containing a tumor-cidal agent coupled with an apoptosis inhibitor with significant in vivo tumor inhibitory effect and clear applicability to human cancer therapeutics.

As disclosed herein, the inventors also administered compositions comprising both (1) siRNA inhibitors of NF=kB, and (2) antibody targeting glut-1 receptors, to both HCT-116 cells and MDA-MB-231 cells (i.e. colon tumor cells, and breast tumor cells, respectively), and examined the effects of the composition on cell viability as compared to normal cell type growth. Using MTT viability assays, higher dosages of composition comprising siRNA inhibitor of NF-kB, and antibody targeting glut-1 receptors (31.7 ug/ml glut-1 Ab, and 8.3 ug/ml NF-kB siRNA) resulted in a decrease in % of cell viability as compared to non-treated cells.

As further disclosed herein, the inventors prepared compositions comprising nanoconjugates (or conjugates) made up of polymeric micelles and one or more antibodies targeting glut-1 conjugated to one or more curcumin molecules. The compositions were administered to both HCT-116 cells and MDA-MB-231 cells (i.e. colon tumor cells, and breast tumor cells, respectively), with and without DOX, and examined the effects of the composition on cell viability as compared to normal cell type growth. The result demonstrated that the addition of the glut-1 antibody onto curcumin micelles, in the presence of DOX in the system, produces significant enhancement to the toxicity and demonstrated that the combination treatment is more effective than if applied in isolation.

In one embodiment, the present invention provides a method of treating a cancer in an individual by administering a therapeutically effective dosage of a composition comprising an inhibitor of an inflammatory pathway and/or a glut antibody to the individual. In another embodiment, the inhibitor of an inflammatory pathway is an inhibitor of NF-kB. In another embodiment, the administration of the composition increases efficacy of additional cancer therapeutics administered to the individual. In another embodiment, the additional cancer therapeutics includes DOX. In another embodiment, the glut antibody is an antibody targeting glut-1. In another embodiment, one or more chemotherapy agents may be added to the composition. In another embodiment, the inhibitor of NF-kB and glut antibody form a nanoconjugate. In another embodiment, the nanoconjugate is delivered as part of a micelle. In another embodiment, the construct further comprises one or more chemotherapy agents. In another embodiment, the nanoconjugate is used as a chemosensitizer prior to chemotherapy. In another embodiment, the individual is a mammal. In another embodiment, the individual is a rodent. In another embodiment, the individual is human. In another embodiment, the inhibitor of NF-kB is one or more siRNA molecules. In another embodiment, the inhibitor of NF-kB is one or more molecules of curcumin. In another embodiment, the glut-1 antibody is toxic to the target. In another embodiment, the cancer is colon cancer. In another embodiment, the cancer is breast cancer. In another embodiment, the cancer is brain cancer. In another embodiment, the tumor is a HCT-116 and/or MDA-MB-231 cell. In another embodiment, the inhibitor of NF-kB is administered at about 8.3 ug/ml. In another embodiment, the inhibitor of NF-kB is administered at more than 8.3 ug/ml. In another embodiment, the glut-1 antibody is administered at about 31.7 ug/ml. In another embodiment, the glut-1 antibody is administered at more than 31.7 ug/ml. In another embodiment, the composition is administered to the individual by direct injection.

In another embodiment, the present invention provides a method of decreasing the size of a tumor by administering a therapeutically effective dosage of a composition comprising an inhibitor of NF-kB and/or a glut-1 antibody to the tumor. In another embodiment, the inhibitor of NF-kB is an siRNA molecule. In another embodiment, the glut-1 antibody is toxic to the tumor. In another embodiment, the tumor is a colon tumor. In another embodiment, the tumor is a breast tumor. In another embodiment, the tumor is in the brain. In another embodiment, the tumor is a HCT-116 and/or MDA-MB-231 cell. In another embodiment, the inhibitor of NF-kB is administered at about 8.3 ug/ml. In another embodiment, the inhibitor of NF-kB is administered at more than 8.3 ug/ml. In another embodiment, the glut-1 antibody is administered at about 31.7 ug/ml. In another embodiment, the glut-1 antibody is administered at more than 31.7 ug/ml.

In another embodiment, the present invention provides a nanoconjugate construct made up of one or more targeting segments, linker segments, and/or NF-kB inhibitors. In another embodiment, the one or more NF-kB inhibitors is made up of curcumin. In another embodiment, the one or more targeting segments is an antibody targeting glut-1.

As readily apparent to one of skill in the art, nanoconjugates and other nanomedicines for cancer treatment benefit from a small size. Vessels that supply tumors often leak and can block delivery of candidate treatments to the tumor. Similarly, nanoconjugates that are too large cannot penetrate tissue. Thus, in accordance with various embodiments described herein, an antibody targeting Glut-1 conjugated to one or more inhibitors of NF-kB, such as curcumin, provides benefits of high efficacy due to a size less than 40 nm. In one embodiment, the nanoconjugate is less than 20 nm. In another embodiment, the nanoconjugate is between 20 nm and 40 nm. In another embodiment, the nanoconjugate is between 20 nm and 60 nm. In another embodiment, the nanoconjugate is between 60 nm and 100 nm.

In various embodiments, the present invention provides pharmaceutical compositions including a pharmaceutically acceptable excipient along with a therapeutically effective amount of composition comprising an inhibitor of Nf-kB and an antibody targeting glut-1. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective composition comprising siRNA encoding Nf-kB and Ab targeting glut-1 or conjugates of curcumin and one or more antibodies targeting glut-1 can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to preparation of and use of a composition comprising one or more inhibitors of Nf-kB and one or more antibodies targeting glut-1. The kit is useful for practicing the inventive method of treating cancer or tumors. The kit is an assemblage of materials or components, including at least one of the inventive compositions.

The exact nature of the components configured in the inventive kit depends on its intended purpose. For example, some embodiments are configured for the purpose of treating a tumor and/or cancer, such as colon or breast cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to decrease or kill a tumor. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Similarly, the various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illus-

Example 1

Experiments Using SiRNA as an NF-kB Inhibitor—Materials siRNA:

```
                                             (SEQ ID NO: 1)
Sense strand sequence: GCCCUAUCCCUUUACGUCAtt[AmC7]

(SEQ ID NO: 2)
AntiSense strand sequence: UGACGUAAAGGGAUAGGGCtt
```

Test Glut-1 Antibodies and siRNA NF-kB (Table 1):

TABLE 1

| Sample Description | Buffer | Conc. by UV (mg/ml) | Aliquots supplied |
|---|---|---|---|
| Anti human glut-1 | PBS | 1 ug/ml | 100 ul |
| siRNA | siRNA Dilution Buffer | 1 ug/ml | 100 ul |
| Positive control Dox | DMSO | 20 mM | 1 ml |

Materials for Cell Culture:
(1) McCoy's 5A medium: Gibco, Invitrogen (Cat #16600)
(2) DMEM medium: Gibco, Invitrogen (Cat #10566)
(3) Fetal Bovine Serum (FBS): Gibco, Invitrogen (Cat #10437-036)
(4) Penicillin-Streptomycin: Gibco, Invitrogen (Cat #10378)
(5) Phosphate-Buffered Saline (PBS): Gibco, Invitrogen (Cat #10010-023)
(6) 384-well plate: Corning (Cat#3707)
Cell Line:
HCT-116 cell line (Cat #CCL-247)
MDA-MB-231 cell line (Cat #HTB-26)

Assay Kit:
CellTiter-Glo Luminescent cell viability Assay kit: Promega (Cat No: G7571)
Detection Device:
PHERAstar Plus: BMG Labtech

Example 2

Experiments Using SiRNA as an NF-kB Inhibitor—Preparation of Cell Culture

Cells Thawing:
The medium were pre-warmed in a 37° C. water bath. A frozen vial of cells was quickly submerged and thawed by gently swirling the vial in the 37° C. water bath. After 1-2 min, the medium in the vial was completely thawed. The outside of the vial was wiped with 70% ethanol. The cell suspension was then transferred to a 15-ml centrifuge tube, followed by addition of 5 ml of pre-warmed complete medium. After centrifugation for 3-5 min at 500 g, the supernatant was aspirated. 10 ml of complete medium was added and the cells were resuspended by pipetting up and down for a few times. Cell viability was determined by Trypan blue exclusion method. The cell suspension was then seeded in a 10-cm cell culture dish. The cells were incubated at 37° C., 5% CO2 overnight.

Cell Culture Maintenance and Subculture:
Cells were maintained at 37° C./5% CO2 and regularly sub-cultured with suitable medium supplemented with 10% FBS. For adherent cell lines, when the cells reached 80%-90% confluence, the medium was aspirated. The cells were washed with PBS briefly and then treated with 0.05% Trypsin-EDTA until cells were detached. 10 ml complete medium was added to terminate the reaction. The cells were counted and then sub-cultured at a split ratio recommended by ATCC. For suspension cell lines, cultures were maintained by addition of fresh medium or replacement of medium according to
protocols from ATCC.

Cell Cryopreservation:
Cells in log phase were harvested to a 15 ml centrifuge tube and centrifuged at 1000 g for 5 min. The supernatant was aspirated and 0.5 ml of freshly-made freezing medium was added. After counting of the cells, the cell density was adjusted to 1× 106 cells/ml. 1 ml aliquots of the cell suspension were transferred into cryopreservation tubes and stored at −80° C.

Example 3

Experiments Using SiRNA as an NF-kB Inhibitor—Table 2—Solution Concentrations Test samples were diluted with Buffer to indicated concentrations as described below (table 2). The solutions were stored at 4° C. in the dark.

TABLE 2

| 2× (Glut-1 antibody solution + siRNA inhibiting NF-kB) mixed solution [ug/ml] | 31.70 + 8.3 | 6.34 + 1.66 | 1.27 + 0.33 | 0.25 + 0.07 | 0.05 + 0.01 |
|---|---|---|---|---|---|

Example 4

Experiments Using SiRNA as an NF-kB Inhibitor—MTT Cell Viability Assay (1) The cells in log-phase were collected and counted. 75 μl cell suspensions were added to each well at a density of 5,000 cells/well. The margin wells were filled with PBS.
(2) The cells were incubated at 37° C./5% CO2 overnight to allow the cells to adhere.
(3) Various concentrations of positive and test compounds were added in triplicate and the cells were incubated at 37° C./5% CO2 for 48 h and 72 h, respectively.

(4) The medium was aspirated and 100 μl of medium without phenol red was added. 10 μl of MTT reagent (stock solution: 5 mg/ml) was added to each well and the cells were incubated for an additional 4 h.
(5) The mixture of medium and MTT reagent was aspirated.
(6) 50 μl of DMSO was added to each well and the plate was agitated on a plate shaker for 10 min to allow complete solubilization of the purple formazan crystals.
(7) The absorbance was read at 540 nm on FlexStation 3.

Example 5

Experiments Using SiRNA as an NF-kB Inhibitor—Results of MTT Assay

Target Cells were seeded into 96-well plate at a density of 5,000/well and then were incubated at 37° C./5% CO2 overnight (20 hours) to allow the cells to adhere. Test samples (2× stock solution) at various concentrations were added in quadruplicate and the cells were incubated at 37° C./5% CO2 for 48 h/72 h. Cell viability was evaluated with MTT assay. The absorbance of each well (O.D. at 540 nM) was measured in MTT viability assay and data was presented as percentage of cell viabilities as compared with the non-treated cells (FIG. 1).

Example 6

Experiments Using SiRNA as an NF-kB Inhibitor—Generally

As disclosed herein, the inventors administered compositions comprising both (1) siRNA inhibitors of NFkB, and (2) antibody targeting glut-1 receptors to HCT-116 cells and MDA-MB-231 cells (i.e. colon tumor cells, and breast tumor cells, respectively), and examined the effects of the composition on cell viability as compared to normal cell type growth. Using MTT viability assays, higher dosages of composition comprising siRNA inhibitor of NFkB, and antibody targeting glut-1 receptors (31.7 ug/ml glut-1 Ab, and 8.3 ug/ml NF-kB siRNA) resulted in a decrease in % of cell viability as compared to non-treated cells.

As described herein, in one embodiment the present invention provides a construct that targets Glut-1 receptor and delivers NF-kB inhibitor to tumor cells. Chemotherapy agents can be added to the construct or the construct can be used as a chemosensitizer prior to chemotherapy. In another embodiment, the construct comprises a targeting segment, a linker, and a NF-kB inhibitor.

Example 7

Glut-1 Targeting

In the interest of balancing construct size and permeability, in one embodiment the glut-1 antibody is a humanized anti-Glut-1 Fab and/or longer peptide. In another embodiment, the anti-Glut-1 antibody is commercially produced.

Example 8

Linker

For linkers, one could use polymer-based (cyclodextrin-based; High-molecular-weight, branched N-(2-hydroxypropyl)methacrylamide (HPMA)) polymeric backbone, or Micelle. In one embodiment, the linker will have the capacity to bind glut-1 targeting antibody (or peptide) plus an effector.

Example 9

NF-kB Inhibitor Effector—Curcumin

Curcumin may serve as a NF-kB inhibitor. As apparent to one of skill in the art, curcumin has NF-kB inhibitory properties with anti-tumor properties and no known toxicity.

Example 10

Inclusion of Chemotherapy Agent

In one embodiment, the construct or composition may also include one or more chemotherapy agents. For example, the construct may include doxorubicin or paclitaxel, which are both effective against breast and lung cancers (before the resistance is induced).

Example 11

Examples of Possible Target Tumor Types

1. MDA-MB-231 Human Hormone-independent Breast Cancer Line
    Expresses both high levels of Glut-1 and constitutive NF-kB.
2. Calu-3 Lung Adenocarcinoma (Non-Small Cell Lung Cancer, NSCLC)
    This line is derived from a patient who was previously treated with chemotherapy, and the induction of chemo resistance is well-known to be mediated by NF-kB in NSCLC.

Both of the above lines represent highly aggressive tumors with high incidence (see table below). Colorectal tumor cell line (HCT 116) is an example of an additional possible target cancer/cell line. Additional cancer types and cell lines, though in no way limited to, include the following:

TABLE 3

| Types of Cancer Cancer Type |
| --- |
| Bladder |
| Breast (Female-Male) |
| Colon and Rectal (Combined) |
| Endometrial |
| Kidney (Renal Cell) Cancer |
| Leukemia (All Types) |
| Lung (Including Bronchus) |
| Melanoma |
| Non-Hodgkin Lymphoma |
| Pancreatic |
| Prostate |
| Thyroid |

Example 12

Animal Models

In one embodiment, subcutaneous implantation of cell lines (such as described in Example 11 above) as xenografts in immunodeficient rodents may be used. In another embodiment, orthotopic animal models of breast/lung or colorectal cancers may also be used.

Example 13

Experiments Using CUR as an NF-kB Inhibitor—Testing the Construct Targeting Glut-1 Receptor and Delivering NF-Kb Inhibitor to Cancer Cells Cell lines used were MDA-MB231 breast cancer cell line and HCT 116 colon adenocarcinoma cell lines. The construct (also known as nanoconjugate) represents PEG-PE-based polymeric micelles (PM) loaded with curcumin (CM) and modified with commercial anti-Glut-1 monoclonal antibody. The construct is tested against two selected cell lines with or without doxorubicin (Dox) being present in the system. IC50 for Dox was preliminary determined for these cells and survival % curves built. The presence of new constructs was found to increase the level of cell death at the same Dox concentration. The following systems were tested in each cell experiment: Ab-PM-CM (the test system); PM-CM; free CM; Ab-PM; Ab; PM, i.e. 6 groups altogether (1 experimental and 5 controls). Two different concentrations of CM were used. The total number of experiments were 12 (with two cell lines; with and without Dox; with two concentrations of Dox; and with two concentrations of CM). In each group the level of cell death was determined. Ab activity after attaching to PM was tested before the experiment using the ELISA test with Glut-1 as the antigen

Example 14

Experiments Using CUR as an NF-kB Inhibitor—Preparation of the CUR-Loaded Micelles CUR (Sigma Aldrich, St. Louis, Mo. catalog #C7727) drug-loaded micelles were prepared by the thin film hydration method. Approximately 1.2 mg of CUR (3 mg/mL in methanol stock solution) was added to 19.35 mg of $PEG_{2000}$-PE dissolved in chloroform at a concentration of 50 mg/mL (Corden Pharma, Switzerland catalog# LP-R4-039). Organic solvents were removed by rotary evaporation, to form a thin film of drug/micelle mixture, which was further dried under high vacuum for at least 4 hours to remove all remaining organic solvents (Freezone 4.5 Freeze Dry System Labconco, Kansas City, Mo.). Drug-loaded micelles are spontaneously formed when the film is resuspended in a polar solvent, in this case 5 mM 4-(2-hydroxyethyl)-1-peperazine-ethanesulfonic acid (HEPES)-buffered saline (HBS), pH 7.4 was used. The mixture was resuspended in 1 mL HBS, incubated in a water bath at 40° C. for 10 min, and then vortexed for a few minutes to insure proper resuspension of the lipid film. Excess non-incorporated drug was separated by centrifugation (13,500 rpm) for 5 minutes followed by filtration through a sterile 0.2 µm syringe filter before characterization (Nalgene, Rochester, N.Y.).

Example 15

Experiments Using CUR as an NF-kB Inhibitor—Preparation of the DOX-Loaded Micelles DOX (Hisun Pharma, Princeton, N.J.) drug-loaded micelles were also prepared by the thin film hydration method. Approximately 2 mg of DOX (2 mg/mL in methanol stock solution) were added to a round bottom flask containing 0.7 mg of triethanolamine (TEA) at a mole ratio of 1:2 DOX:TEA and then vortexed. This step produces the free base of DOX, which easily incorporates into the micelle. After a 5 minute incubation period at room temperature, 19.35 mg of $PEG_{2000}$-PE in chloroform at a mole ratio of 1:2 DOX:$PEG_{2000}$-PE was added and vortexed. To make the lipid film, organic solvents were removed by rotary evaporation then dried under high vacuum for at least 4 hours to remove all remaining organic solvents (Freezone 4.5 Freeze Dry System Labconco, Kansas City, Mo.). DOX-loaded micelles were formed by resuspension in 1 mL 5 mM HBS, pH 7.4. The solution was then dialyzed using a 2000 Da MWCO membrane against 1 L of HBS pH 7.4 for 4 hours to remove TEA and the free DOX. The micelles were then filtrated through a sterile 0.2 µm syringe filter before characterization for sterility (Nalgene, Rochester, N.Y.).

Example 16

Experiments Using CUR as an NF-kB Inhibitor—Preparation of the GLUT1-Targeted Micelles To attach the GLUT1 antibody (Santa Cruz Biotechnology, Santa Cruz, Calif.) to the micelles a pNP-$PEG_{3400}$-PE polymer was synthesized. The activated p-nitrophenylcarbonyl (pNP) group at the distal end of the $PEG_{3400}$-PE monomer reacts with amino-groups of various ligands yielding a stable urethane (carbamate) bond. Synthesis of this polymer was achieved according to standardized in-lab procedures. Briefly, pNP-$PEG_{3400}$-pNP and DOPE were dissolved in dry chloroform, co-incubated with TEA and then reacted at RT under Argon with continuous stirring overnight. Solvents were then removed by rotary evaporation and films were further dried under vacuum for at least 4 hours to remove all residual solvents. The dried films were then rehydrated with 0.001M HCl (pH3.0) and separated on a sepharose (CL4B) column. Fractions were collected and analyzed by TLC to identify aliquots containing the pNP-$PEG_{3400}$-PE product; these fractions were then frozen, lyophilized, weighed and reconstituted with chloroform to appropriate stock concentrations, and stored at −80° C. for further use.

To attach GLUT1 to micelles, $PEG_{2000}$-PE in chloroform was supplemented with 5 mole % of the reactive polymer, pNP-$PEG_{3400}$-PE in chloroform, with or without CUR, and then vortexed for complete mixing. Chloroform was then evaporated under a rotary evaporator to form a thin film. Films were further dried under vacuum overnight to remove any residual solvents. The solution was then rehydrated with 5 mM Na-citrate buffered saline pH 5.0 to insure the lipid film is completely dispersed. The stock GLUT1 antibody in PBS pH 7.4 was then added at a mole ratio 40:1 pNP-$PEG_{3400}$-PE:Antibody and then the pH of solution was further adjusted with PBS pH 10.0 to ~8.5. Reaction time was ~4 hrs at room temperature, to allow sufficient GLUT1 antibody conjugation and complete hydrolysis of unreacted pNP groups at the higher pH. GLUT1-micelles were then dialyzed using a 300,000 MWCO membrane against 1 L 1×PBS (pH 7.4) for 1 hr followed by another 4 hrs of dialysis in 4 L 1×PBS (pH 7.4) to insure the complete removal of unconjugated GLUT1 antibody.

Conjugation efficiency of GLUT1 antibody was measured using a micro BCA kit (Pierce, Rockford, Ill.) according to the manufacture's manual. Protein content was determined by comparing GLUT1-micelles to a known concentration of antibody and BCA standards. Signals from GLUT1 antibody samples were normalized with plain micelle samples at the same lipid concentration.

Example 17

Experiments Using CUR as an NF-kB Inhibitor—Characterization of the Micellar Formulations Drug incorporation efficiency was measured by reverse phase HPLC using an Xbridge $C_{18}$ column (Waters Corporation, Milford, Mass.) on a Hitachi Elite LaChrome HPLC equipped with an autosampler (Pleasanton, Calif.) and diode array detector. A gradient method was used with mobile phase consisting of acetonitrile, water supplemented with 0.2% TFA, and methanol. The flow rate used was 1 mL/min (Refer to FIG. 1 for more details). DOX was detected at wavelengths of 254 and 485 nm, while CUR was detected at 420 nm. Sample injection volume was kept constant at 50 μL and the sample run time was 20 min. Concentration of drug was determined by measuring the area under curve of the corresponding peaks. Standard curves of stock drug solution, dissolved in the mobile phase, were used to determine the concentration of incorporated drug in micelles. Ten microliters of drug-loaded micelles were diluted in 990 μL of the mobile phase to disrupt the micelles and release entrapped drug for detection. All samples were analyzed in triplicate. Separation of peaks for both drugs was achieved with DOX and CUR detected at 5.247 and 13.953 minutes respectively. The standard curves obtained for DOX and CUR from the HPLC method had an $R^2$ value of 0.999 (n=3). This method was developed to detect DOX and CUR in the same micellar formulation. DOX elutes in the initial stage where the mobile phase is relatively polar; whereas CUR elutes at the later stage of the gradient method when the mobile phase is less polar.

TABLE 4

| Time (minutes) | A: Acetonitrile (% v/v) | B: Water with 0.2% TFA (% v/v) | C: Methanol (% v/v) |
|---|---|---|---|
| 0 | 25 | 50 | 25 |
| 7 | 25 | 50 | 25 |
| 8.5 | 40 | 40 | 20 |
| 10 | 60 | 30 | 10 |
| 11.5 | 80 | 20 | 0 |
| 13 | 100 | 0 | 0 |
| 16 | 100 | 0 | 0 |
| 17 | 25 | 50 | 25 |
| 20 | 25 | 50 | 25 |

Example 18

Experiments Using CUR as an NF-kB Inhibitor—In Vitro Activity of Drug-Loaded Micelles Two cell lines were used in these experiments, HCT-116 and MDA-MB231 cell lines. The cells were grown according to the propagation procedures provided by ATCC. Viability of cells was measured using the Cell Titer-Blue (Promega, Madison, Wis.) viability assay according to the manufacture's protocol. Briefly, cells were seeded in 96-well plates at a density of 5,000 cells/well and grown for 24 hrs. They were then continuously incubated with the various formulations for 48 hrs in serum complete media. After 48 hrs of treatment, media was removed and cells were washed with 200 μL serum complete media, then incubated with 100 μL media containing 20 μL Cell Titer-Blue reagent. Cell viability was evaluated after ~2 hrs of incubation, by measuring the fluorescence (excitation 530 nm, emission 590 nm) with the Synergy HT multi-detection microplate reader (Biotek, Winooski, Vt.). Untreated cells were taken as controls to calculate percent cell viability and treatment was carried out in triplicate.

It is important to note that empty $PEG_{2000}$-PE micelles, empty GLUT1-targeted micelles, methanol, and free GLUT1 antibody had minimal cytotoxic effects on the cells at the corresponding concentrations used.

Example 19

In Vivo

The inventors prepared various micelle compounds as cancer therapeutics and tested them in vivo. In one embodiment, the inventors prepared a cancer therapeutic construct based on a nano-sized lipid carrier encapsulating a cell-toxic chemotherapy molecule combined with an inhibitor of tumor chemo-resistance, targeted to tumor cells by tumor-recognizing antibody on its surface. Studies using chemotherapy-resistant colon and breast cancer lines in-vitro and in mouse xenografts showed significant tumor growth suppression, with almost no tumor growth seen (as compared to over 300% increase in tumor volume in control animals). Additionally, the construct was developed to be of optimal molecular size and biophysical properties in order to deliver clinically meaningful drug quantities in a whole animal setting, while avoiding toxicity associated with intravenous chemotherapy treatment.

The effects of various components of therapeutic constructs were studied as follows. Mice were implanted subcutaneously with HCT-116 colon adenocarcinoma cells and those in whom tumor mass volume reached 250 mm$^3$ were included in the study. The animals with the implanted tumors were divided into six (6) groups (with 6 mice per group) and treated with one of the following:
  Phosphate Buffered Saline (Control group)—(PBS Control)
  Anti-Glut1 Antibody (Ab) linked to empty micelle—(Glut1-Empty Micelles)
  Micelles containing Curcumin at a dose of 4 mg/kg—(Cur Micelles)
  Anti-Glut1 Ab linked to Curcumin-containing micelles—(Glut1-Cur Micelles)
  Micelles containing Doxorubicin (0.4 mg/kg) and Curcumin—(Cur+Dox Micelles)
  The complete compound, Anti-Glut1 Ab linked to micelles containing Doxorubicin (0.4 mg/kg) and Curcumin—Glut1-Cur+Dox Micelles.

Each group of mice was given 7 total intravenous injections every other day starting on Day 0. The tumor volume in each group of animals was measured on Day 12. The results were as follows:
  The control group, treated with PBS only, showed a 180% increase in tumor volume on Day 12 as compared with Day 0
  Glut1-Empty Micelles group showed a 100% increase in tumor volume
  Cur Micelles group showed a 140% increase in tumor volume
  Glut1-Cur Micelles group showed a 46% increase in tumor volume size Cur+Dox Micelles group showed a 86% increase in tumor volume and Glut1-Cur+Dox Micelles group showed just 6% increase in tumor volume.

The tumor inhibitory effects of various components were clearly additive, with the complete compound showing the most dramatic, almost complete, inhibition of tumor growth at Day 12 time point. It is noteworthy, that the tumor inhibitory effect grew in size as each additional component was being added to the experimental construct. The data also showed that the combination of anti-Glut1 Ab and curcumin-loaded micelles was the second most potent formulation in tumor growth suppression. Cur+Dox micelles and Glut1A-linked empty micelles showed similar tumor suppressing effect, at approximately ½ of the effect of the complete compound. Another conclusion drawn from the present study was that the effect on tumor growth suppression observed in vivo paralleled very closely results obtained from previous in vitro studies by the inventors. Specifically, the same additive effects of various compound components on tumor growth suppression were seen in vitro, enabling the inventors to draw general conclusions about the mechanism of action of the compound described by the present application.

In one embodiment, the present invention provides a method of treating cancer and/or inhibiting growth in a tumor cell in a subject, by providing a composition comprising a micelle targeted by glut-1 receptor antibody and attached to curcumin and/or dox, and administering a therapeutically effective dosage to the subject. In another embodiment, the composition is administered to the subject intravenously.

In accordance with an embodiment further described herein, by utilizing dox attached to a targeted micelle as a lipid-based delivery vehicle, rather than liposomal dox, or just dox, for example, the inventors created a cancer treatment with significantly high penetration of tumor mass. In addition to creating high tumor mass penetration, administering a composition comprising a dox attached to a targeted micelle optimized intracellular delivery of dox within the tumor cell itself. Because dox acts as a weakly basic compound, if it enters a low pH environment, or the lysosome of a tumor cell for example, the dox can lose much of its effectiveness for inhibiting tumor cell growth. By administering dox attached to a targeted micelle, rather than administering liposomal dox for example, the inventors enabled the dox to instead enter the cytoplasm, thus optimizing intracellular delivery. Additionally, dox can have high toxicity which can thus limit its practical application in vivo and usefulness as a cancer treatment for human subjects. In contrast, the inventors administered dox attached to a targeted micelle, resulting in further optimization of its effectiveness as a cancer therapeutic.

In accordance with various embodiments further disclosed herein, the inventors also attached curcumin to a targeted micelle. Due to its nonsoluble properties, if administered directly, curcumin must be administered at high concentrations to be effective inhibiting tumor growth. However, at those same high concentrations, curcumin results in high toxicity, thus making it an impractical and ineffective cancer treatment in vivo, and particularly difficult for use in human patients. In accordance with an embodiment herein, by attaching curcumin to a targeted micelle, treatment can be administered at a significantly lower dosage, thus reducing toxicity while effectively inhibiting tumor growth.

As compared to the liposomal forms of both doxorubicin and curcumin, a micellar preparation is of significantly smaller molecular size (10-20 nm vs. 80-150 nm liposomes) resulting in improved tumor mass penetration from the vascular bed, thus creating a more effective cancer therapeutic. Additionally, in accordance with an embodiment herein, the addition of the Glut-1 Ab to the micelle greatly increased its therapeutic efficacy over the un-targeted micelle preparations through improved intracellular delivery of its contents. Glut-1 presents an attractive extracellular target since it is one of the main glucose transporters involved in tumor glucose uptake. Solid tumors can take up glucose at much higher rates than do normal cells. Glycolysis represents a main source of energy and carbon building blocks for growing tumors. Thus, in accordance with an embodiment herein, a micelle construct with a Glut-1 Ab is an effective cancer therapeutic, as glut-1 overexpression will persist even in the face of tumor phenotypic evolution, and it will be difficult for tumors to mutate away from glut-1 overexpression and still retain their high growth potential. In regard to using glut-1 as the tumor targeting entity, by binding to the tumor membrane-overexpressed glut-1, various embodiments of therapeutic micelles described herein get endocytosed into the cytoplasm rather than the low-pH lysosome, thereby increasing the therapeutic efficacy of doxorubicin (which has much lower activity at low pH).

Since the tumor lines used in these experiments were doxorubicin-resistant, it was critical that curcumin delivery occurred contemporaneously with doxorubicin exposure in order for it to exert its tumoricidal effect. As NF-kappa B overexpression and its attendant apoptosis- and chemotherapy-resistance are present in advanced cancers, the inventors designed various embodiments herein to include an NF-kappa B inhibitor (for example, curcumin) in order to unlock the cidal effect of doxorubicin. In one embodiment, the present invention is a tumor-targeted micelle containing a tumor-cidal agent coupled with an apoptosis inhibitor with significant in vivo tumor inhibitory effect and clear applicability to human cancer therapeutics.

Example 20

In Vivo Methods—Testing the Construct Targeting GLUT1 Receptor and Delivering

NF-Kb Inhibitor to Cancer Cells

Materials 1,2-Distearoyl-sn-glycero-3-phosphoethanolamine-N-[methoxy(polyethylene glycol)-2000] ($PEG_{2000}$-DSPE) was purchased from CordenPharma International (Plankstadt, Germany); 1,2-dioleoyl-sn-glycero-3-phosphoethanolamine (DOPE) was purchased from Avanti Polar Lipids (Alabaster, Ala., USA) and used without further purification; pNP-$PEG_{3400}$-pNP was purchased from Laysan Bio (Arab, Ala.). Curcumin (CUR) was purchased from Sigma (St. Louis, Mo., USA catalog #C7727). Doxorubicin (DOX) free base was purchased from US Biological (Swampscott, Mass.). GLUT1 (C-20) sc-1605 antibody was purchased from Santa Cruz Biotechnology, Inc. (Santa Cruz, Calif.). Matrigel® basement membrane matrix was purchased from BD Biosciences (Bedford, Mass.). All other reagents and buffer solution components were analytical grade preparations. Distilled and deionized water was used in all experiments.

Preparation of the Drug-Loaded Micelles

CUR and/or DOX drug-loaded micelles were prepared by the thin film hydration method. Specific amounts of CUR (3 mg/mL in methanol stock solution) and/or DOX free base (0.5 mg/mL in methanol stock solution) were added to PEG$_{2000}$-PE in chloroform. The concentration of the micelle-forming material used in all experiments was 5 mM. Organic solvents were removed by rotary evaporation, to form a thin film of drug/micelle mixture, which was further dried under high vacuum overnight to remove all remaining organic solvents (Freezone 4.5 Freeze Dry System Labconco, Kansas City, Mo.). Drug-loaded micelles are spontaneously formed by when the film is resuspended in a polar solvent, in this case 1× phosphate buffer saline pH 7.4 was used. The mixture was incubated in a water bath at 40° C. for 10 min and then vortexed for at least 5 minutes to insure proper resuspension of the lipid film. Excess non-incorporated drugs were separated by centrifugation (13,500 g) for 5 minutes followed by filtration through a sterile 0.2 µm syringe filter before characterization (Nalgene, Rochester, N.Y.).

Preparation of the GLUT1-Targeted Micelles

To attach the GLUT1 antibody to the micelles, a pNP-PEG$_{3400}$-PE polymer was synthesized. The activated p-nitrophenylcarbonyl (pNP) group at the distal end of the PEG$_{3400}$-PE monomer reacts with amino-groups of various ligands yielding a stable urethane (carbamate) bond. Synthesis of this polymer was achieved according to standardized in-lab procedures. Briefly, pNP-PEG$_{3400}$-pNP and DOPE were dissolved in dry chloroform, co-incubated with TEA and then reacted at RT under Argon with continuous stirring overnight. Solvents were then removed by rotary evaporation and films were further dried under vacuum for at least 4 hours to remove all residual solvents. The dried films were then rehydrated with 0.001M HCl (pH 3.0) and separated on a sepharose (CL4B) column. Fractions were collected and analyzed by TLC to identify aliquots containing the pNP-PEG$_{3400}$-PE product; these fractions were then frozen, lyophilized, weighed and reconstituted with chloroform to appropriate stock concentrations, and stored at −80° C. for further use.

To attach GLUT1 to micelles, the reactive polymer, pNP-PEG$_{3400}$-PE in chloroform was added to a round bottom flask. Chloroform was evaporated under a rotary evaporator to form a thin film. Films were further dried under vacuum overnight to remove any residual solvents, rehydrated with stock GLUT1 solution in 1×PBS (pH 7.4) at a molar ratio of pNP-PEG-PE:GLUT1 40:1. The pH of the solution was adjusted with 1.0 N NaOH to 8.5 as needed. Reaction time was 4 hrs at room temperature, to allow sufficient GLUT1 conjugation and complete hydrolysis of unreacted pNP groups at the higher pH. GLUT1 micelles were then dialyzed using a 300,000 MWCO membrane against 1×PBS (pH 7.4) for 1 hr followed by another 4 hrs of dialysis in 1×PBS (pH 7.4) to insure the complete removal of unconjugated antibody. Targeted combination micelles were prepared by co-incubating drug-loaded micelles with GLUT1-modified micelles at a ratio of 2 mole % of the reactive polymer, pNP-PEG$_{3400}$-PE, to PEG$_{2000}$-PE. Samples were vortexed and allowed to mix for at least 4 hours at room temperature.

Conjugation efficiency of GLUT1 antibody was measured using a micro BCA kit (Pierce, Rockford, Ill.) according to the manufacture's manual. Protein content was determined by comparing GLUT1-micelles to a known concentration of antibody and BCA standards. Signals from GLUT1 antibody samples were normalized with plain micelle samples at the same lipid concentration.

Characterization of the Micellar Formulations

Drug incorporation efficiency was measured by reverse phase HPLC using an Xbridge C$_{18}$ column (Waters Corporation, Milford, Mass.) on a Hitachi Elite LaChrome HPLC equipped with an autosampler (Pleasanton, Calif.) and diode array detector. A gradient method was used with mobile phase consisting of acetonitrile, water supplemented with 0.2% TFA, and methanol. The flow rate used was 1 mL/min (Refer to FIG. 1 for more details). DOX was detected at wavelengths of 254 and 485 nm, while CUR was detected at 420 nm. Sample injection volume was kept constant at 504 and the sample run time was 20 min. Concentration of drug was determined by measuring the area under curve of the corresponding peaks. Standard curves of stock drug solution, dissolved in the mobile phase, were used to determine the concentration of incorporated drug in micelles. Ten microliters of drug-loaded micelles were diluted in 990 µL of the mobile phase to disrupt the micelles and release entrapped drug for detection. All samples were analyzed in triplicate. Separation of peaks for both drugs was achieved with DOX and CUR detected at 5.247 and 13.953 minutes respectively. The standard curves obtained for DOX and CUR from the HPLC method had an $R^2$ value of 0.999 (n=3). This method was developed to detect DOX and CUR in the same micellar formulation. DOX elutes in the initial stage where the mobile phase is relatively polar; whereas CUR elutes at the later stage of the gradient method when the mobile phase is less polar.

TABLE 5

| Time (minutes) | A: Acetonitrile (% v/v) | B: Water with 0.2% TFA (% v/v) | C: Methanol (% v/v) |
|---|---|---|---|
| 0 | 25 | 50 | 25 |
| 7 | 25 | 50 | 25 |
| 8.5 | 40 | 40 | 20 |
| 10 | 60 | 30 | 10 |
| 11.5 | 80 | 20 | 0 |
| 13 | 100 | 0 | 0 |
| 16 | 100 | 0 | 0 |
| 17 | 25 | 50 | 25 |
| 20 | 25 | 50 | 25 |

Cell Culture

HCT-116 human colon cancer cells (CCL-247®) were purchased from ATCC (Manassas, Va.) and maintained in McCoy's 5A medium (ATCC 302007®) supplemented with 10% heat-inactivated fetal calf serum, penicillin, streptomycin, and amphotericin from CellGro (Kansas City, Mo.). Cells were maintained at 37° C. in a humidified incubator with 5% CO$_2$, and were passaged according to ATCC protocols.

In Vivo Xenograft Model

Six-week-old female NU/NU nude mice were purchased from Charles River Laboratories International Inc. (Needham, Mass.). HCT 116 cell suspensions (5×10$^6$ cells/0.2 mL PBS:Matrigel 1:1 v/v) were injected subcutaneously into the right flank of each mouse. Mice were treated when their tumor volume reached ~250 mm$^3$ 15 days after tumor inoculation. Animals were randomly divided into six groups (six animals per group). Doxorubicin (0.4 mg/kg) and Curcumin (4 mg/kg) were injected IV every other day for a total of 7 injections. Tumor volume was estimated from measurements in two perpendicular dimensions taken manually with vernier calipers by applying the formula (L×W$^2$)/2, where L is the longest dimension and W is perpendicular to L.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of treating breast cancer or colon cancer in a subject, comprising:
   providing a composition comprising a micelle construct attached to curcumin at a concentration of 4 mg/kg,
   wherein the micelle construct is attached to doxorubicin at a concentration of 0.4 mg/kg,
   wherein the micelle construct is targeted to bind to glut-1 by using a glut-1 antibody as a targeting agent; and
   administering a therapeutically effective dosage of the composition to the subject.

2. The method of claim 1, wherein the micelle construct is less than 30 nm.

3. The method of claim 1, wherein the subject is a human.
4. The method of claim 1, wherein the subject is a mouse.
5. The method of claim 1, wherein the cancer is colon cancer; and
   the micelle construct is 50 nm or less,
   wherein the combination of anti-glut-1 antibody linked to micelles containing doxorubicin and curcumin have a synergistic effect to treat the colon cancer.
6. The method of claim 1, wherein the cancer is a chemotherapy-resistant cell.

* * * * *